United States Patent [19]

Ghisalba et al.

[11] Patent Number: 4,490,471
[45] Date of Patent: Dec. 25, 1984

[54] MICROORGANISMS OF THE GENUS PSEUDOMONAS AND PROCESS FOR DEGRADING COMPOUNDS WHICH CONTAIN METHYL GROUPS IN AQUEOUS SOLUTIONS

[75] Inventors: Oreste Ghisalba, Basel; Franz Heinzer, Porrentruy; Martin Küenzi, Muttenz, all of Switzerland

[73] Assignee: Ciba-Geigy Corporation, Ardsley, N.Y.

[21] Appl. No.: 446,736

[22] Filed: Dec. 3, 1982

[30] Foreign Application Priority Data

Dec. 11, 1981 [CH] Switzerland ............... 7933/81

[51] Int. Cl.$^3$ ............... C12N 1/20; C12N 1/32; C07 ; C12R 1/38
[52] U.S. Cl. ............... 435/253; 435/247; 435/262; 435/874
[58] Field of Search ............... 435/247, 262, 253; 210/611, 612

[56] References Cited

U.S. PATENT DOCUMENTS 4,317,843 3/1982 MacLennan et al. ......... 435/247 X

OTHER PUBLICATIONS

Chem. Abstracts, vol. 92, No. 3, Item 20540d.
Chem. Abstracts, vol. 88, No. 19, Item 134840z.
Wagner et al. Journal of Bacteriology, Jun. 1975, pp. 905-910.
Rock et al., Agr. Biol. Chem., vol. 40 (11), 2129-2135 (1976).
Chem. Abstracts, vol. 90, No. 26, Item 209493r.
Mackrell et al., Int. Biodeterior Bull., vol. 14 (3) 1978, pp. 77-83.
Chemical Abstracts vol. 81, No. 16 (96040j-k).
Hampton et al., Biochem. Transactions, vol. 1 pp. 667-668 (1973).
Colby et al., Biochem. J., vol. 148 (1975) pp. 505-511.

*Primary Examiner*—Lionel M. Shapiro
*Attorney, Agent, or Firm*—Michael W. Glynn

[57] ABSTRACT

The present invention relates to novel facultative methylotrophic microorganisms of the genus Pseudomonas, or of a genus Pseudomonas-type genus, to protein-containing biomass, and to a process for the microbiological purification of aqueous solutions, e.g. wastewater solutions, which contain methanol, ethanol, acetate, glucose, alkylammonium compounds, e.g., trimethylethylammonium chloride, or alkylamine oxides, e.g. trimethylamine oxide, as pollutants.

7 Claims, No Drawings

MICROORGANISMS OF THE GENUS PSEUDOMONAS AND PROCESS FOR DEGRADING COMPOUNDS WHICH CONTAIN METHYL GROUPS IN AQUEOUS SOLUTIONS

The present invention relates to novel facultative methylotrophic microorganisms of the genus Pseudomonas, or of a Pseudomonas-type genus, to a process for the microbiological purification of aqueous solutions by degrading compounds which contain methyl groups in the presence of said microorganisms, to the biomass which is produced by said microorganisms, and to the use of the biomass obtained by the process of this invention.

The term "methylotrophic microorganisms" shall be understood as meaning those microorganisms which grow on nutrient media containing, as carbon source, compounds having only one carbon atom, e.g. methanol.

The term "facultative methylotrophic microorganisms" shall be understood as meaning those microorganisms which grow on nutrient media containing, as carbon source, compounds having one carbon atom, e.g. methanol, and/or compounds having several carbon atoms, e.g. glucose.

There are described in the literature facultative methylotrophic microorganisms which, in aqueous solution, are able to degrade or to utilise as carbon source, or as carbon and nitrogen source, one or more compounds selected from the group of organic compounds consisting of: methanol, ethanol, acetates, e.g. sodium acetate, monosaccharides, e.g. glucose, disaccharides, e.g. saccharose, specific methylammonium compounds, e.g. trimethylammonium chloride, ethylmethylammonium chloride or ethyldimethylammonium chloride, and the free amines thereof, or trimethylamine oxide.

Such microorganisms are deposited in various culture collections, e.g. in the American Type Culture Collection (ATCC), in the Deutsche Sammlung von Microorganismen (DSM), or in the National Collection of Industrial Bacteria (NCIB), and are listed in the catalogues published by these collections.

A number of facultative methylotrophic microorganisms which grow in aqueous solution in the presence of tetramethylammonium chloride are described by J. Colby and by L. J. Zatmann, Biochem. J., 148, 505-511 (1975), and by D. Hampton and L. J. Zatmann in Biochem. Soc. Trans. 1, 667-668 (1973), without mentioning a culture collection. These microorganisms are, moreover, not listed in any of the catalogues published by culture collections.

The degradability of quaternary ammonium compounds, e.g. trimethylethylammonium chloride, in aqueous solution by microorganisms is described by Y. A. Mackrell and J. R. L. Walker in Int. Biodeterior. Bull. 14(3), 1978 (77-83). There is no characterisation of the microorganisms concerned in this publication, nor are there any particulars relating to their origin, to the method of isolation and to the culture collection.

Large-scale production in the chemical industry gives rise to the formation of aqueous solutions, e.g. wastewaters, which contain these compounds and/or trimethylethylammonium chloride, as pollutants, in some cases in very high concentrations. In order to prevent these compounds (salts) from becoming an environmental nuisance, such wastewaters have to be purified. However, purification creates very serious problems. For example, lower alkylammonium salts, e.g. trimethylammonium chloride or the free amines corresponding to these salts, have up to now been eliminated by incineration. In general, the incineration of organic waste must regarded in the long term as a very unsatisfactory method of elimation which incurs high costs and also creates severe environmental problems.

This problem is solved by the prevent invention, which relates to novel facultative methylotrophic microorganisms of the genus Pseudomonas, or of a Pseudomonas-type genus, which microorganisms are able to degrade all the compounds mentioned above and, in particular, trimethylethylammonium chloride. The invention also relates to a process for the microbiological purification of aqueous solutions by degradation of lower alkanols, lower alkanoates, monosaccharides, disaccharides, methylammonium compounds of the formula

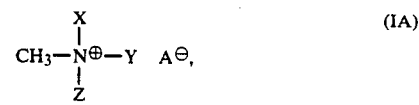

wherein $A^\ominus$ is an anion, X is hydrogen or methyl, each of Y and Z is hydrogen, methyl or ethyl, with the proviso that X is hydrogen if Y and Z are ethyl, or of free amines corresponding to these salts, and of methylamine oxides of the formula

wherein X is hydrogen or methyl and Y is hydrogen, methyl or ethyl, and mixtures of said compounds, in the presence of said microorganisms, to the biomass which is produced by these microorganisms, and also to the use of the biomass obtained by the process of the invention.

Throughout this specification, the definitions of compounds generally employed preferably have the following meanings: lower alkanols are e.g. methanol or ethanol; lower alkanoates are e.g. salts of acetic acid, e.g. sodium acetate or potassium acetate; monosaccharides are e.g. hexoses, e.g. glucose, and also fructose, mannose or galactose; disaccharides are e.g. saccharose, maltose or lactose.

An anion $A^\ominus$ is e.g. an anion which is non-toxic to the microorganism employed and suitable for the degradation process, e.g. a halide ion such as the fluoride or bromide ion, preferably the chloride ion, or the acetate, nitrate, sulfate or phosphate ion.

The present invention relates in particular to microorganisms of the genus Pseudomonas, or of a Pseudomonas-type genus, and to a process for the microbiological purification of aqueous solutions by degradation of methanol, ethanol, sodium acetate or potassium acetate, glucose, methylammonium compounds of the formula IA, wherein $A^\ominus$ is the chloride ion, X and Y are hydrogen or methyl and Z is hydrogen, methyl or ethyl, trimethylamine oxide of the formula IB, or mixtures of said compounds.

More particularly, the invention relates to microorganisms of the genus Pseudomonas selected from the group of the following strains: Pseudomonas TMEA 14 (NRRL-B-12582), TMEA 81 (NRRL-B-12581), TMEA 83 (NRRL-B-12580), TMEA 84 (NRRL-B-12579), TMEA 86 (NRRL-N-12578), TMEA 87 (NRRL-B-12577), TMEA 89 (NRRL-B-12576), TMEA 199 (NRRL-B-12755) and TMEA 211 (NRRL-B-12574), and to a process for the microbiological purification of aqueous solutions by degradation of methylammonium compounds of the formula IA, wherein $A^\ominus$ is the chloride ion, X and Y are hydrogen or methyl and Z is hydrogen, methyl or ethyl, of trimethylamine oxide of the formula IB, or of mixtures of said compounds.

Most particularly, the present invention relates to microorganisms of the genus Pseudomonas selected from the group of the following strains: Pseudomonas TMEA 14 (NRRL-B-12582), TMEA 81 (NRRL-B-12581), TMEA 83 (NRRL-B-12580), TMEA 84 (NRRL-B-12579), TMEA 86 (NRRL-B-12578), TMEA 87 (NRRL-B-12577), TMEA 89 (NRRL-N-12576), TMEA 199 (NRRL-B-12575) and TMEA (NRRL-B-12574), and to a process for the microbiological purification of aqueous solutions by degradation of trimethylethylammonium chloride.

The novel microorganisms originate from the sludge of a wastewater purification plant of Ciba-Geigy AG (WPP-CG) and were deposited with the Agricultural Research Culture Collection (NRRL) in Peoria, Ill. 61604, USA, on Nov. 3, 1981 under the Budapest Treaty on the International Recognition of the Deposit of Microorganisms for the Purposes of Patent Procedure. Deposit number and method of isolation of each individual strain are indicated in Table 1.

TABLE 1

| Designation | | Deposit No. | Method of |
|---|---|---|---|
| Genus | Strain No. | (NRRL) | isolation |
| Pseudomonas | TMEA 14 | B-12582 | 1 |
| Pseudomonas | TMEA 81 | B-12581 | 1 |
| Pseudomonas | TMEA 83 | B-12580 | 1 |
| Pseudomonas | TMEA 84 | B-12579 | 1 |
| Pseudomonas | TMEA 86 | B-12578 | 1 |
| Pseudomonas | TMEA 87 | B-12577 | 1 |
| Pseudomonas | TMEA 89 | B-12576 | 1 |
| Pseudomonas | TMEA 199 | B-12575 | 2 |
| Pseudomonas | TMEA 211 | B-12574 | 2 |

Method 1: A sample of wastewater or a sludge suspension (1 g per 10 ml of sterile water) is plated out on sterile agar (based on MV 7 nutrient solution) which contains trimethylethylammonium chloride. The MV 7 nutrient solution contains, in one litre of water, the following ingredients: 2 g of $NH_4NO_3$ (nitrogen source), 1.4 g of $Na_2HPO_4$, 0.6 g of $KH_2PO_4$ (buffer and phosphorus source), 0.2 g of $MgSO_4.7H_2O$, 0.01 g of $CaCl_2.2H_2O$, 0.001 g of $FeSO_4.7H_2O$, and 1 ml of a trace element solution (consisting of 20 mg/1 of each of $Na_2MoO_4.2H_2O$, $Na_2B_4O_7.10H_2O$, $MnSO_4.H_2O$, $ZnSO_4.H_2O$ and $CuSO_4.5H_2O$.

The salts are dissolved in distilled water, the solution is adjusted to pH 7 with dilute NaOH and made up to 1 litre with distilled water. The solid MV 7 agar culture medium is prepared by adding a further 20 g/1 of agar (Difco) to the nutrient solution. Sterilisation is effected in an autoclave. Incubation is carried out at 28°–30° C. Single colonies are cautiously picked and streaked again on the same medium. This procedure is repeated a number of times until pure isolates are obtained.

Method 2: A sample of wastewater or a sludge suspension (1 g per 10 ml of sterile water) is put into a shaking bottle containing sterile MV 7 nutrient solution. An aqueous solution of trimethylethylammonium chloride which is filtered under sterile conditions is added, and the batch is incubated for 14 days at 28° C. as stationary culture or for 7 days at 250 rpm as shake culture. Then 0.5 ml of this first enrichment culture is added to the fresh MV7 nutrient solution and again incubated at 28° C. as stationary culture or shake culture. Then 0.5 ml of this second enrichment culture is in turn added to the fresh nutrient solution and incubation is carried out for 7 days at 28° C. The second and third enrichment culture is plated out on sterile MV 7 agar which contains trimethylethylammonium chloride [MV 7 nutrient solution with the addition of 20 g/1 of agar (Difco)] and incubated at 28° C. Single colonies are cautiously picked and streaked again on the same medium. This procedure is repeated several times until pure isolates are obtained.

CHARACTERISATION OF THE NOVEL MICROORGANISMS

1. General parameters and microscopy

All the strains listed in Table 1 are gram-negative, oxidasepositive, and grow best under aerobic conditions at 28° to 30° C. As sources of carbon they are able to utilise alkylammonium compounds of the formula IA, alkylamine-N-oxides of the formula IB, as well as a number of other organic compounds, e.g. methanol (only the strains Pseudomonas TMEA 14 and 199), ethanol (only the strains Pseudomonas TMEA 14, 81, 83, 84, 87, 89, 199 and 211) as well as acetate, e.g. sodium acetate, and glucose. Because of these properties, the novel microorganisms are suitable for the process for the microbiological purification of those aqueous solutions which contain these carbon sources as pollutants.

Under microscopic observation (optical microscope), all the strains are very similar and appear as motile rods about 1–2 μ long which occur individually, in pairs or in agglomerates. The electron microscope image accords well with the findings made by optical microscopy. All the strains are also very similar, with two types of cell in particular being observed:

(a) plump to oblong rods with 1–2 subpolar flagellae and in some cases very fine hairs on the surface of the cell, (b) the other type of cell has the same characteristics as (a), but has no flagellae.

2. Biochemical characterisation and classification of the novel microorganisms (a) "Oxi/Ferm Tube" Assay (Roche)

This assay is used for gram-negative rods with positive oxidase reaction. The assay is carried out in parallel once with cells of the respective strain taken from trimethylethylammonium chloride-agar and from nutrient-agar. The experiment is carried out in accordance with the manufacturer's instructions. The test results are set forth in Table 2.

Two commercially available assays are employed for the general biochemical characterisation and classification of the strains listed in Table 1.

TABLE 2

TMEA Strains tested with "Oxi/Ferm Tube" (48 h, 28° C.)

Biochemical assay

| Strain No. | anaerobic dextrose cleavage | arginine dihydrolase | $N_2$ production | $H_2S$ formation | indole formation | xylose cleavage | aerobic dextrose cleavage | urease | citrate utilization |
|---|---|---|---|---|---|---|---|---|---|
| TMEA 14  | − | −    | −*  | − | − | − | − | ± | − |
| TMEA 81  | − | −(*) | +   | − | − | ± | ± | + | + |
| TMEA 83  | − | −(*) | ±*  | − | − | ± | ± | ±(*) | + |
| TMEA 84  | − | −    | −*  | − | − | − | − | −  | ±(*) |
| TMEA 86  | − | −*   | −*  | − | − | + | + | ± | −* |
| TMEA 87  | + | −    | ±*  | − | − | + | + | −(*) | ±* |
| TMEA 89  | − | −(*) | +   | − | − | ± | ± | + | ±* |
| TMEA 199 | − | −    | +   | − | − | − | − | + | + |
| TMEA 211 | − | −    | +   | − | − | − | − | + | + |

+ both parallel assays positive
− both parallel assays negative
± one assay positive, one assay negative
* positive in the API 20 E assay
(*) in the API 20 E assay ±

From the test results reported in Table 2 and from their numerical evaluation it is possible to group the individual strains into four categories according to the degree to which their common characteristics vary and to classify them approximately as follows by numerical code:

TABLE 3

| Strain No. | Common characteristics | Group | Classification |
|---|---|---|---|
| TMEA 14 and 84 | similar | I | Pseudomonas-like or Pseudomonas species |
| TMEA 86 and 87 | similar | II | Pseudomonas-like or Pseudomonas species |
| TMEA 81, 83 and 89 | very similar | II | Achromobacter Species or Pseudomonas species |
| TMEA 199 and 211 | identical | III | Achromobacter species or Alcaligenes feacalis |

(b) API 20E Assay

The assay is carried out in parallel once with cells of the relevant strain from trimethylethylammonium chloride/agar and from nutrient/agar. The procedure is in accordance with the manufacturer's instructions. The results are set forth in Table 4.

TABLE 4

TMEA Strains tested with API 20E (48 h, 28° C.)

| | Biochemical assay | TMEA 14 | TMEA 81 | TMEA 83 | TMEA 84 | TMEA 86 | TMEA 87 | TMEA 89 | TMEA 199 | TMEA 211 |
|---|---|---|---|---|---|---|---|---|---|---|
| CAT: | catalase | + | + | + | + | + | + | + | + | + |
| $N_2$: | nitrate reduction | + | + | + | + | + | + | + | + | + |
| $NO_2$: |  | + | + | + | + | + | + | + | + | + |
| OX: | oxidase | +w | + | + | + | + | +s | + | + | + |
| ARA: | L-arabinose utilisation | ± | − | − | − | − | + | − | − | − |
| AMY: | amygdaline utilisation | + | − | − | + | − | + | ± | − | − |
| MEL: | melibiose utilisation | − | − | − | − | + | + | − | − | − |
| SAC: | saccharose utilisation | ± | − | − | + | − | + | ± | − | − |
| RHA: | rhamnose utilisation | ± | − | − | − | − | + | − | − | − |
| SOR: | sorbitol utilisation | − | − | − | − | − | + | − | − | − |
| INO: | inositol utilisation | − | − | − | − | − | + | − | − | − |
| MAN: | mannitol utilisation | − | − | − | − | − | + | − | − | − |
| GLU: | glucose utilisation | − | − | − | ± | ± | + | − | − | − |
| GEL: | gelatin utilisation | − | − | ± | − | − | + | − | − | − |
| VP: | acetoin test | ± | − | − | ± | ± | ± | ± | ± | ± |
| IND: | tryptophan degradation indole formation | − | − | − | − | − | − | − | − | − |
| TDA: | tryptophan desaminase | − | − | − | − | − | − | − | − | − |
| URE: | urease | ± | ± | ± | − | −(*) | ± | ± | + | + |
| $H_2S$: | thiosulfate cleavage | − | − | − | − | − | − | − | − | − |
| CIT: | citrate utilisation | ± | + | ± | ± | + | + | + | + | + |
| ODC: | ornithine decarboxylase | − | − | − | − | − | + | − | − | − |
| LDC: | lysine decarboxylase | − | − | − | − | − | + | ± | − | − |
| ADH: | arginine dihydrolase | − | ± | ± | − | + | − | ± | − | − |
| ONPG: | hydrolysis by | ± | + | + | + | − | + | + | ± | − |

TABLE 4-continued

| | TMEA Strains tested with API 20E (48 h, 28° C.) | | | | | | | | |
|---|---|---|---|---|---|---|---|---|---|
| | Strain No. | | | | | | | | |
| Biochemical assay | TMEA 14 | TMEA 81 | TMEA 83 | TMEA 84 | TMEA 86 | TMEA 87 | TMEA 89 | TMEA 199 | TMEA 211 |
| β-galactosidase | | | | | | | | | |

+ both parallel assays positive
− both parallel assays negative
± one assay positive, one assay negative
(*) one assay positive in the Oxi/Ferm Tube assay (w = weak)
OX (cytochromoxidase) in H₂S and ONPG
CAT: in MAN, INO and SOR The test results in Table 4 permit the individual strains to be classified into the following groups:
I': TMEA 14 and 84 are very similar,
II': TMEA 81, 83 and 89 are very similar,
III': TMEA 199 and 211 are virtually identical.
Strains 86 and 87 are probably single strains.

The numerical evaluation of the API 20 E assay does not permit any unequivocal classifications to be made, so that the results reported in Table 4 can only be used for characterising the respective strains.

(c) Comparison of the two assays a) and b)

The following cross-comparisons can be made respecting the nine strains listed in Table 1:

H₂S formation and indole formation are always negative in both systems. Urease and citrate utilisation are in relatively good accord in both assays. The different findings with respect to arginine dihydrolase and N₂ production are explained by the greater sensitivity of the measurements in the API 20 E assay.

The biochemical data of the novel microorganisms listed in Table 1, i.e. the results of the Oxi/Ferm Tube assay and the API 20 E assay, which permit an approximate classification of the novel microorganisms as Pseudomonas species, Pseudomonas-like, Achromobacter species or Alcaligenes faecalis, are in accord with the features described for such microorganisms in "Bergey's Manual of Determinative Bacteriology" (8th Edition) in the section entitled "Gramnegative Aerobic Rods and Cocci". As Achromobacter species and Alcaligenes faecalis to all intents and purposes do not differ biochemically from Pseudomonas species and the transitions between the genera are gradual, the designation "Pseudomonas" will be chosen for all microorganisms of this invention on account of the characteristic feature of the polar to subpolar flagellation.

PRESERVATION OF THE STRAINS

The following methods are suitable for preserving the strains of Table 1:

(a) adsorption of the cells of the respective strain onto glass beads in glycerol solution and subsequent storage at −20° C., (b) keeping the cells of the respective strain on slant agar, and (c) lyo-ampoules. The respective culture is centrifuged off from the nutrient solution and the biomass is resuspended in ¼ to ⅓ volumes of 15% skim milk and lyophilised.

The strains listed in Table 1 are able to form mutants spontaneously or to give rise to the artificial production of mutants, which mutants are also able, like the natural strains, to degrade lower alkanols, e.g. methanol or ethanol, lower alkanoates, e.g. sodium acetate, monosaccharides, e.g. glucose, disaccharides, e.g. saccharose, methylammonium compounds of the formula IA, e.g. trimethylethylammonium chloride, or methylamine-N-oxides of the formula IB, e.g. trimethylamine-N-oxide, in aqueous solution, and to produce biomass. Such mutants can be produced by chemical means, e.g. with certain guanidine derivatives, e.g. N-methyl-N'-nitro-N-nitrosoguanidine, or with alkali nitrite, e.g. sodium nitrite, or by physical means, e.g. by ultraviolet, X-ray or radioactive radiation.

The microorganisms of this invention are used in a process for the microbiological purification of aqueous solutions, which process comprises culturing in an aqueous solution containing lower alkanols, lower alkanoates, monosaccharides, disaccharides, methylammonium compounds of the formula IA, wherein $A^\ominus$, X, Y and Z have the meanings previously assigned to them, or the free amines corresponding to these salts, methylamine oxides of the formula IB, wherein X and Y have the meanings previously assigned to them, a microorganism of the genus Pseudomonas, or of a genus similar to Pseudomonas, which microorganism is able to produce biomass characterised by a multiple of the approximate empirical formula $C_5H_9NO_2$ and containing 44.67% by weight of carbon, 7.04% by weight of hydrogen, 10.50% by weight of nitrogen, 25.00% by weight of oxygen, 1.12% by weight of phosphorus and 0.33% by weight of sulfur (lyophilised), as well as about 8% water content, and also a mutant derived from said microorganism which is suitable for the process and also produces said biomass, in the presence of nutrient inorganic salts and optionally of a nitrogen source, in the temperature range from about 20° to 40° C. and in a pH range from about 4 to 7.5, and, if desired, isolating the resultant biomass.

During the culturing or fermentation, the strains listed in Table 1 are able to degrade the ingredients present in aqueous solution, e.g. in a wastewater, said ingredients being e.g. methanol, ethanol, sodium acetate, glucose, and, in particular, alkylammonium compounds of the formula IA or alkylamine oxides of the formula IB or mixtures of said compounds, and to consume oxygen. The microorganisms listed in Table 1 are able to degrade these ingredients in some cases in very high concentrations of the compounds or salts concerned. During the degradation, the microorganisms produce biomass characterised by a multiple of the empirical formula $C_5H_9NO_2$ and containing 44.67% by weight of carbon, 7.04% by weight of hydrogen, 10.50% by weight of nitrogen, 25.00% by weight of oxygen, 1.12% by weight of phosphorus and 0.33% by weight of sulfur, as well as about 8% by weight of water (lyophilised). Carbon dioxide, ammonium salts of the formula $NH_4^\oplus A^\ominus$, e.g. ammonium chloride, and the acid HA, e.g. hydrogen chloride, are formed as further fermentation products. The pH will be adjusted to values from about 4 to 7.5, preferably from about 5 to 6, by addition of a buffer solution, e.g. phosphate buffer solution, or of an aqueous base, e.g. aqueous sodium or potassium hydroxide solution.

The strains TMEA 14 or 199 will be used for purifying methanol-containing aqueous solutions, and the strains TMEA 14, 81, 83, 84, 87, 89, 199 and 211 will be used for purifying ethanol-containing aqueous solutions.

Fermentation is carried out in the presence of nutrient inorganic salts. Such salts are e.g. halides, e.g. chlorides, carbonates, sulfates or phosphates or alkali metals, alkaline earth metals or transition metals, as well as borates or molybdates of alkali metals.

Examples of preferred nutrient inorganic salts are disodium or dipotassium hydrogen phosphate, sodium or potassium dihydrogen phosphate, magnesium or iron sulfate, and potassium and calcium chloride. Zinc sulfate, manganese sulfate and copper sulfate, sodium molybdate and borax can additionally be added in small amounts.

For purifying aqueous solutions which contain e.g. methanol, ethanol, acetate or glucose, and which therefore do not contain nitrogen-containing compounds, there are added as nitrogen source, e.g. amino acids, peptides or proteins or their degradation products such as peptone, or tryptone, meat extracts, flours, e.g. corn flour, wheat flour or bean flour, e.g. soybean flour, distillation residues of alcohol production, yeast extracts and, preferably, ammonium salts, e.g. ammonium chloride, or nitrates, e.g. potassium nitrate or ammonium nitrate.

Culturing is effected under aerobic conditions, e.g. with the introduction of oxygen or air and with shaking or stirring in shaking bottles or fermenters. Culturing can be effected in the temperature range from about 25° to 35° C., preferably from about 27° to 28° C.

Culturing can be carried out batchwise, e.g. by single or repeated addition of nutrient solution; or continuously, by continuous addition of nutrient solution.

It is preferred to effect culturing in several stages by first preparing one or more precultures, e.g. in a liquid nutrient medium, with which precultures the main culture batch is then inoculated. A preculture may be prepared e.g. by inoculating a sterile nutrient solution, e.g. MV 7 containing a suitable carbon source, e.g. trimethylethylammonium chloride, with a sample of cells of the microorganism concerned, which is kept e.g. on slant agar, and incubating the batch for several days at 28° C. A fresh nutrient solution, e.g. MV 7 containing the same carbon source, is inoculated with this first preculture and the batch is incubated for several days at 28° C.

In order to monitor the course of the fermentation analytically, samples can be taken e.g. for measuring the pH of the culture or the optical density, which is a reference value for the growth of the strain in question, as well as for the gravimetric analysis on the basis of the dry weight of the biomass obtained.

Finally, the resultant biomass can be processed e.g. by one of the numerous methods described in European patent specification No. 0 010 243 and converted e.g. into fertiliser.

Biomass is defined in this context as comprising all cell systems in the living state, e.g. that of replication or resting, in the state of partial or complete death, or already in a state of enzymatic decomposition or of decomposition by foreign cultures, which cell systems are based on th microorganisms of this invention.

This biomass is a valuable raw material which has a defined and reproducible composition. It has the approximate empirical formula $C_5H_9NO_2$ and contains (lyophilisate): 44.67% by weight of carbon, 7.04% by weight of hydrogen, 10.50% by weight of nitrogen, 25.00% by weight of oxygen, 1.12% by weight of phosphorus and 0.33% by weight of sulfur, as well as about 8% water content.

The biomass obtained by the process of this invention can be used in the form of single cell protein having a defined and reproducible composition as cattle feed additive. The biomass can also be used as suspension or processed to fertiliser, e.g. after dehydration or pasteurisation. The biomass can also be used as starting material for the production of biogas with a high heat content (composition: about 70% of methane, 29% of carbon dioxide and 1% of hydrogen, heat content about 5500-6500 kcal/m$^3$), for example by anaerobic fermentation in fermentation towers. The residue (sludge) from the process for the production of biogas is also a high-grade fertiliser which, compared with the original biomass, is highly enriched with nitrogen. The invention is illustrated by the following Examples.

EXAMPLE 1

(Preparation of the preculture)

1 sample of cells of the microorganism of strain TMEA 199, which is kept on slant agar, is introduced into a shaking bottle containing 20 ml of MV 7 nutrient solution which has the composition as indicated above together with 5 g/l of trimethylethylammonium chloride and the batch is incubated for 72 hours at 28° C. and 250 rpm. Then 5-7 mm of this first preculture are introduced into a second shaking bottle containing 100 ml of MV 7 nutrient solution (without ammonium nitrate), 5 g/l of trimethylethylammonium chloride and 5 mmoles of phosphate buffer of pH 7, and the batch is incubated for 72 hours at 28° C. and 250 rpm.

EXAMPLE 2

Precultures of the strains TMEA 14, 81, 83, 84, 86, 87, 89 or 211 can be prepared as described in Example 1.

EXAMPLE 3

In a laboratory fermenter, 10 litres of optionally heat-sterilised MV 7 nutrient solution (without ammonium nitrate; sterilisation for 20 minutes at 120° C.) and trimethylethylammonium chloride which is optionally filtered under sterile conditions, are combined to give an approximate total volume of 10 litres having a concentration of about 10 g/l of trimethylethylammonium chloride. A sample of about 500 ml of the second preculture of the strain TMEA 199 is added and the following conditions are maintained: pH 5.5, kept constant by adding, as required, 4N NaOH or 1N HCl; temperature 28° C.; air supply 0.26 l/min; stirring rate 400-700 rpm.

The strain grows on pure trimethylethylammonium chloride as sole source of carbon and nitrogen. The trimethylethylammonium chloride is completely degraded after about 200 hours. The biomass obtained is in the form of a mixture of single cells or aggregates of different size which can be separated by sedimentation or centrifugation.

EXAMPLE 4

Trimethylethylammonium chloride can be degraded in aqueous solution as described in Example 3 by growing precultures of the strains TMEA 14, 81, 83, 84, 86, 87, 89 or 211 in a laboratory fermenter.

EXAMPLE 5

In a laboratory fermenter, 10 litres of heatsterilised MV 7 nutrient solution (without ammonium nitrate; sterilisation for 20 minutes at 120° C.) are combined with a wastewater solution filtered under sterile conditions and containing trimethylethylammonium chloride (composition: 45.2% of trimethylethylammonium chloride, 6.4% of HCl, 47.5% of water and less than 1% of aromatic compounds) so as to give a total volume of about 10 litres having a concentration of about 10 g/l of trimethylethylammonium chloride. A sample of about 500 ml of the second preculture of the strain TMEA 199 is added and the conditions described in Example 3 are kept. Degradation of the substrate is complete over the course of 190 hours.

EXAMPLE 6

Trimethylethylammonium chloride can be degraded in wastewater solutions filtered under sterile conditions in accordance with Example 5 by growing precultures of the strains TMEA 14, 81, 83, 84, 86, 87, 89 or 211 in a laboratory fermenter.

EXAMPLE 7

In the manner as described in Examples 5 and 6, trimethylethylammonium chloride can be degraded in waste-water solutions, omitting the filtration under sterile conditions, by cultivating the precultures of the strains TMEA 14, 81, 83, 84, 86, 87, 89, 199 or 211 in a laboratory fermenter.

What is claimed is:

1. A biologically pure culture of microorganisms of the genus Pseudomonas or of Pseudomonas-type genus selected from the group of the following strains:
   Pseudomonas NRRL-B-12582,
   Pseudomonas NRRL-B-12581,
   Pseudomonas NRRL-B-12580,
   Pseudomonas NRRL-B-12579,
   Pseudomonas NRRL-B-12578,
   Pseudomonas NRRL-B-12577,
   Pseudomonas NRRL-B-12576,
   Pseudomonas NRRL-B-12575,
   Pseudomonas NRRL-B-12574, and mutants thereof.

2. A process for the microbiological purification of aqueous solutions by degradation of lower alkanols, lower alkanoates, monosaccharides, disaccharides, methylammonium compounds of the formula

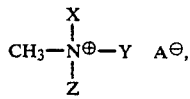

wherein $A^\ominus$ is an anion, X is hydrogen or methyl, each of Y and Z is hydrogen, methyl or ethyl, with the proviso that X is hydrogen if Y and Z are ethyl, or the free amines corresponding to these salts, or methylamine oxides of the formula

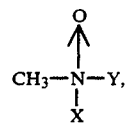

wherein X is hydrogen or methyl and Y is hydrogen, methyl or ethyl, or mixtures of said compounds, which process comprises culturing in such an aqueous solution a microorganism of the genus Pseudomonas according to claim 1 and a mutant thereof which is able to produce biomass characterized by a multiple of the approximate empirical formula $C_5H_9NO_2$ and containing 44.67% by weight carbon, 7.04% by weight hydrogen, 10.50% by weight nitrogen, 25.00% by weight oxygen, 1.12% by weight phosphorus and 0.33% by weight sulfur (lyophilized), as well as about 8% water content, in the presence of nutrient inorganic salts and optionally of a nitrogen source, in the temperature range from about 20° to 40° C. and in a pH range from about 4 to 7.5, and, if desired, isolating the biomass obtained.

3. A process according to claim 2 for the microbiological purification of aqueous solutions by degradation of methanol, ethanol, sodium acetate or potassium acetate, glucose, methylammonium compounds of the formula IA, wherein $A^\ominus$ is chloride, X and Y are hydrogen or methyl and Z is hydrogen, methyl or ethyl, or of mixtures of said compounds, which process comprises culturing in such an aqueous solution a miroorganism of the genus Pseudomonas according to claim 1 or mutants thereof.

4. A process according to claim 3 for the microbiological purification of aqueous solutions by degradation of methylammonium compounds of the formula IA, wherein $A^\ominus$ is chloride, X and Y are hydrogen or methyl and Z is hydrogen, methyl or ethyl, of trimethylamine oxide of the formula IB or of mixtures of said compounds, which process comprises culturing in such an aqueous solution a microorganism selected from the group of the following strains:
   Pseudomonas NRRL-B-12582,
   Pseudomonas NRRL-B-12581,
   Pseudomonas NRRL-B-12580,
   Pseudomonas NRRL-B-12579,
   Pseudomonas NRRL-B-12578,
   Pseudomonas NRRL-B-12577,
   Pseudomonas NRRL-B-12576,
   Pseudomonas NRRL-B-12575 and
   Pseudomonas NRRL-B-12574.

5. A process according to claim 2 for the microbiological purification of aqueous solutions by degradation of trimethylethylammonium chloride of the formula IA, which process comprises culturing in such an aqueous solution a microorganism selected from the group of the following strains:
   Pseudomonas NRRL-B-12582,
   Pseudomonas NRRL-B-12581,
   Pseudomonas NRRL-B-12580,
   Pseudomonas NRRL-B-12579,
   Pseudomonas NRRL-B-12578,
   Pseudomonas NRRL-B-12577,
   Pseudomonas NRRL-B-12576,
   Pseudomonas NRRL-B-12575 and
   Pseudomonas NRRL-B-12574.

6. A process according to claim 2, wherein culturing the microorganism is carried out at 28° C.

7. A process according to claim 2, wherein culturing the microorganism is carried out batchwise.

* * * * *